(12) United States Patent
Ellman et al.

(10) Patent No.: US 6,210,409 B1
(45) Date of Patent: Apr. 3, 2001

(54) ELECTROSURGICAL HANDPIECE FOR TREATING TISSUE

(76) Inventors: Alan G. Ellman; Jon C. Garito, both of 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/393,286

(22) Filed: Sep. 10, 1999

Related U.S. Application Data

(63) Continuation-in-part of application No. 09/303,839, filed on May 3, 1999.

(51) Int. Cl.[7] .................................................. A61B 18/18
(52) U.S. Cl. ................................ 606/41; 606/48; 606/49; 606/51; 606/52
(58) Field of Search .................................. 607/96, 98, 99, 607/101, 115, 116; 606/32, 39, 40, 41, 45, 46, 47, 48, 49, 50, 51, 52

(56) References Cited

U.S. PATENT DOCUMENTS 5,441,499 * 8/1995 Fritzsch ................................. 606/45
5,709,224 * 1/1998 Behl et al. .............................. 128/898
6,010,500 * 1/2000 Sherman et al. ........................ 606/41

* cited by examiner

*Primary Examiner*—Linda C. M. Dvorak
*Assistant Examiner*—R. Kearney

(57) ABSTRACT

An electrosurgical handpiece that is bipolar in operation and that is configured for use in minimally invasive surgery (MIS). The bipolar operation confines the electrosurgical currents to a small active region between the active ends of the bipolar electrode and thus reduces the possibility that excessive heat will be developed that can damage patient tissue. The position of the active region can be controlled to avoid patient tissue that may be more sensitive to excessive heat. In one embodiment, the electrosurgical electrode ends are configured as parallel prongs spaced apart to embrace a blood vessel. In another embodiment, the electrosurgical electrode ends are configured as one straight and one hooked prong to more easily embrace a blood vessel. The handpiece is constructed with a flexible end controllable by the surgeon so as to allow the surgeon to manipulate the end as desired during the surgical procedure.

6 Claims, 1 Drawing Sheet

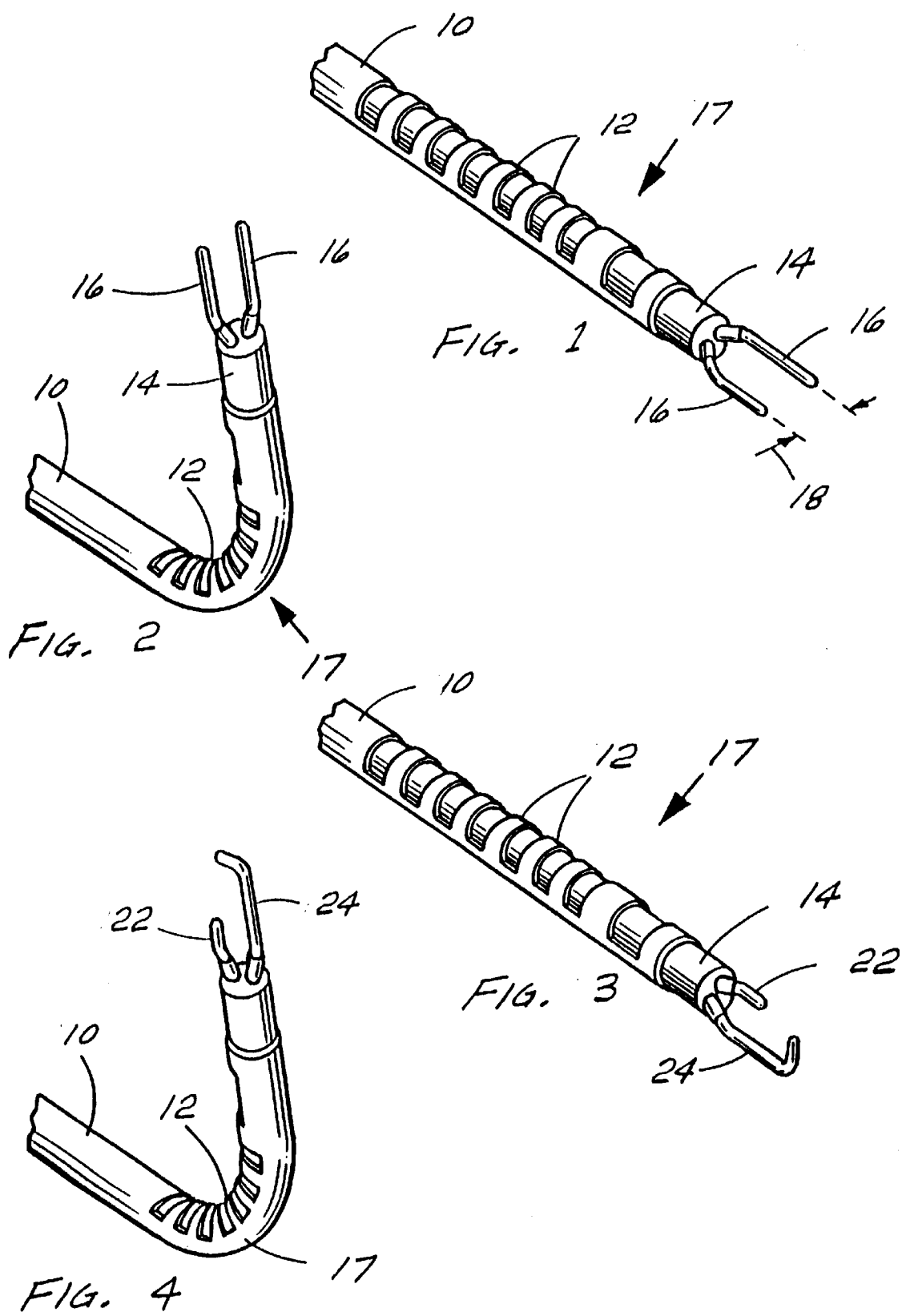

ELECTROSURGICAL HANDPIECE FOR TREATING TISSUE

RELATED APPLICATION

U.S. application, Ser. No. 09/303,839, filed May 3, 1999, commonly owned, for "Electrosurgical Handpiece For Treating Tissue", of which the present application is a continuation-in-part.

This invention relates to electrosurgical electrodes for use in an electrosurgical handpiece and an activator for an electrosurgical handpiece.

BACKGROUND OF THE INVENTION

Our prior application, Ser. No. 09/303,839, describes a novel electrosurgical handpiece for treating tissue in a surgical procedure commonly known as minimally invasive surgery (MIS). Among the features described and claimed in the prior application is an electrosurgical handpiece that can be used in MIS and reduces the danger of excessive heat causing possible patient harm. This is achieved in one embodiment by an electrosurgical handpiece that is bipolar in operation and that is configured for use in MIS. The bipolar operation confines the electrosurgical currents to a small active region between the active ends of the bipolar electrode and thus reduces the possibility that excessive heat will be developed that can damage patient tissue. Moreover, the position of the active region can be controlled to avoid patient tissue that may be more sensitive to excessive heat. Preferably, the handpiece is provided with a dual compartment insulated elongated tube, each of the compartments serving to house one of the two wires of the bipolar electrodes. The electrode for MIS use is preferably constructed with a flexible end controllable by the surgeon so as to allow the surgeon to manipulate the end as desired during the surgical procedure. In a preferred embodiment, the flexible end is achieved by weakening at the end the housing for the electrode, and providing a pull string or wire connected to the weakened housing end and with a mechanism at the opposite end for the surgeon to pull the string or wire to flex the housing end to the desired position. This feature allows the surgeon to position the active electrode end at the optimum location for treating, say, a herniated disk to remove undesired regions and to provide controlled heat to shrink the tissue during surgery. In FIGS. 3–7 of the prior application, a suitable bipolar electrode is described. FIG. 12 illustrates how such an electrode can be used for the reduction of herniated disks in a laparoscopic procedure. FIG. 20 shows a scissors end that can be constructed as a bipolar electrode for certain purposes.

SUMMARY OF THE INVENTION

The present invention is a continuation-in-part of the prior application and hereby incorporates by reference the total contents of the prior application. The present invention describes two additional bipolar electrodes for use in the handpiece of the prior application but otherwise makes use of the same teachings, and for this reason it was felt unnecessary to repeat in the body of this specification the total the contents of the prior application. The present description will be confined solely to the differences in the electrode ends to achieve certain benefits that may be more difficult to achieve with the electrode constructions of the prior application. For the convenience of the reader, however, attached herewith as Appendix A is a copy of the prior application as filed together with a copy of its drawings. When and if the prior application becomes an issued patent, it is proposed to substitute a copy of the issued patent for the application of Appendix A.

The two new bipolar electrodes of the present improvement are configured to provide hemostasis or cauterization of a bleeder. For this purpose, the electrode ends comprise two electrically-insulated, adjacent, prong-like elements whose ends are laterally spaced apart a distance sufficient to embrace a typical blood vessel in a patient. A preferred spacing is about 2 mm. The spaced prongs project from the flexible end of its tubular housing, and can be positioned by moving the tubular housing and flexing the tubular housing tip to surround or flank the blood vessel to be cauterized by the surgeon manipulating the tubular housing and flexible tip as described in the prior application.

In a first preferred embodiment, the prong ends are straight and lie in a plane extending substantially perpendicular to the plane of flexing. In a second preferred embodiment, one prong end is straight and the other forms a hook lying in a plane extending substantially parallel to the plane of flexing.

The present invention also makes use of the interchangability of electrodes. As explained in connection with FIG. 1 of the prior application, the various bipolar electrodes can be withdrawn from the handpiece and replaced by another bipolar or unipolar electrode enabling the surgeon, without having to remove the handpiece from the cannula, to successively use one or more bipolar or unipolar electrodes as needed. So, for example, after first using a bipolar or unipolar electrode for a cutting procedure, either of the electrodes of the present invention can be substituted to perform hemostasis of any blood vessels cut during the procedure.

The construction of the invention will provide the same important benefits not only for MIS of herniated disks but also for other MIS procedures where controlled electrode position and controlled heat generation is of importance as described in the prior application.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 1 is a perspective view of the working end of one form of a bipolar activator according to the invention for use with an electrosurgical handpiece as described in the prior application. The working end is shown in its non-flexed position;

FIG. 2 is a view similar to that of FIG. 1 with the working end shown in one of its possible flexed positions;

FIG. 3 is a perspective view of the working end of another form of a bipolar activator according to the invention for use with an electrosurgical handpiece as described in the prior application. The working end is shown in its non-flexed position;

FIG. 4 is a view similar to that of FIG. 3 with the working end shown in one of its possible flexed positions.

DETAILED DESCRIPTION OF THE PREFERRED EMBODIMENTS

The reader is directed to Appendix A for a detailed description of the prior application which will assist in understanding the improvements offered by the present application.

The gun configuration remains the same. The only changes made are the construction of the bipolar electrode end. As in the earlier application, two electrically-insulated wires (not shown) are passed through insulated compartments (not shown) of a tubular housing 10 (FIG. 1) whose end is weakened as by spaced slots 12. A third wire (also not shown) is connected to the housing end such that when the wire is pulled by the surgeon, the housing end can be flexed as shown in FIG. 2. The two wires are not only insulated from each other so that bipolar electrosurgical currents can be applied between them, but they are also insulated from the tubular housing 10 which may be of metal. The latter insulation may be in the form of a flexible plastic tube 14. The two wires terminate in a pair of metal prongs 16 which project from the end of the plastic tube 14 in parallel relationship. The prong ends are laterally spaced from one another, indicated by 18, a distance sufficient to surround on opposite sides a blood vessel. A spacing 18 of about 2 mm is preferred. The surgeon can manipulate the position of the electrodes by pulling on the flexing wire. FIG. 2 illustrates one possible position of the prong ends 16 when the flexible tip 17 is bent. It will be noted that, in this embodiment, the plane of flexing, shown vertical in FIG. 2, is approximately perpendicular to the plane occupied by the two prongs 16, shown horizontal in FIG. 1.

In the variant shown in FIGS. 3 and 4, the prong ends are oriented in a vertical plane, and when the electrode end 17 is flexed, the plane of flexing, vertical in FIG. 4, is parallel to the plane of orientation, vertical in FIG. 3. This demonstrates that the prong ends can be oriented in various planes with respect to the plane of flexing. The orientation is thus not critical. In the FIG. 3 variant, one projecting prong 22 is short, and the other projecting prong 24 is longer and the end 26 is hooked back toward the short projecting prong 22. This hook arrangement may make it easier in certain circumstances to trap and embrace a blood vessel which needs cauterization.

Once the surgeon has positioned the prong ends around the blood vessel, he or she then activates the electrosurgical apparatus causing a bipolar discharge between the bare prong ends and causing cauterization of the blood vessel in the usual way. Other usable mechanical or electrical structures following the teachings of the prior application will be appreciated by those skilled in this art. As with the embodiments of the prior application, the insulating tube 14 will prevent accidental touching of patient tissue by the prong sides, so that the bipolar discharge is localized to the spacings, between the prong ends.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. In an electrosurgical bipolar handpiece comprising an elongated tubular first member having a first end and a remote flexible second end, an elongated tubular second member located within the first member, with said second member comprising an electrically-insulating tube having a first end and a remote flexible second end adjacent the first member's second end and comprising electrically-insulating means dividing the second tube into first and second compartments, and with first and second electrically-conductive wires each positioned, respectively, in the first and second compartments and electrically-insulated from each other, and with first means connected to the first member at its first end for applying electrosurgical bipolar currents to the first and second wires, and second means connected to the first member at its first end for selectively flexing the remote flexible end of the first member relative to the first end of the first member together with the remote flexible end of the second member, and further comprising electrically-insulated electrosurgical electrodes connected to the first and second wires and extendable at the remote flexible end, such that said electrosurgical electrodes can flex together with the remote flexible ends when the second means is operated while maintaining them electrically-insulated, the improvement comprising:

(a) said electrosurgical electrodes comprising first and second bare prongs laterally spaced apart by a distance approximating the size of a blood vessel in a living patient.

2. In an electrosurgical bipolar handpiece for MIS use comprising an elongated tubular first member having a first end and a remote flexible second end, an elongated tubular second member located within the first member, with said second member comprising an electrically-insulating tube having a first end and a remote flexible second end adjacent the first member's second end and comprising electrically-insulating means dividing the second tube into first and second compartments, and with first and second electrically-conductive wires each positioned, respectively, in the first and second compartments and electrically-insulated from each other, and with first means connected to the first member at its first end for applying electrosurgical bipolar currents to the first and second wires, and second means connected to the first member at its first end for selectively flexing the remote flexible end of the first member relative to the first end of the first member together with the remote flexible end of the second member, and further comprising electrically-insulated electrosurgical electrodes connected to the first and second wires and extendable at the remote flexible end, such that said electrosurgical electrodes can flex together with the remote flexible ends when the second means is operated while maintaining them electrically-insulated, the improvement comprising:

(a) said electrosurgical electrodes comprising first and second bare prongs laterally spaced apart by a distance approximating the size of a blood vessel in a living patient.

3. An electrosurgical handpiece for MIS use as claimed in claim 2, wherein the prongs are straight and of about the same length and spaced apart a distance approximately equal to 2 mm.

4. An electrosurgical handpiece for MIS use as claimed in claim 3, wherein the prongs extend in a specific plane, and the tubular member is configured such that, when the second means is activated, the flexible end flexes in a plane substantially perpendicular to the specific plane.

5. An electrosurgical handpiece for MIS use as claimed in claim 2, wherein the the prongs comprise a first prong and a second prong with the second prong extending further away from the tubular housing that the first prong.

6. An electrosurgical handpiece for MIS use as claimed in claim 5, wherein the prongs extend in a specific plane, and the tubular member is configured such that, when the second means is activated, the flexible end flexes in a plane substantially parallel to the specific plane.

* * * * *